US010799620B2

(12) United States Patent
Xie et al.

(10) Patent No.: US 10,799,620 B2
(45) Date of Patent: Oct. 13, 2020

(54) RING AND TUBULAR STRUCTURES AND METHODS OF SYNTHESIS AND USE THEREOF

(71) Applicant: BOARD OF REGENTS OF THE UNIVERSITY OF NEBRASKA, Lincoln, NE (US)

(72) Inventors: Jingwei Xie, Omaha, NE (US); Shixuan Chen, Omaha, NE (US); Bernard Timothy Baxter, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 16/307,711

(22) PCT Filed: Jul. 21, 2017

(86) PCT No.: PCT/US2017/043233
§ 371 (c)(1),
(2) Date: Dec. 6, 2018

(87) PCT Pub. No.: WO2018/017929
PCT Pub. Date: Jan. 25, 2018

(65) Prior Publication Data
US 2019/0192741 A1  Jun. 27, 2019

Related U.S. Application Data

(60) Provisional application No. 62/365,023, filed on Jul. 21, 2016.

(51) Int. Cl.
*A61L 27/54* (2006.01)
*A61L 27/18* (2006.01)
(Continued)

(52) U.S. Cl.
CPC .......... *A61L 27/54* (2013.01); *A61K 31/7068* (2013.01); *A61L 27/18* (2013.01);
(Continued)

(58) Field of Classification Search
CPC .... A61L 27/54; A61L 27/18; A61L 2300/406; A61L 2300/41; A61L 2300/416;
(Continued)

(56) References Cited

U.S. PATENT DOCUMENTS 6,653,005 B1   11/2003   Muradov
7,704,740 B2    4/2010   Schindler et al.
(Continued)

FOREIGN PATENT DOCUMENTS

WO   2016/053988 A1   4/2016
WO   2018/064281 A1   4/2018

OTHER PUBLICATIONS

Liu, Y., et al., "Composite vascular scaffold combining electrospun fibers and physically-crosslinked hydrogel with copper wire-induced grooves structure" J. Mech. Behav. Biomed. Mater. (2016) 61:12-25.
(Continued)

*Primary Examiner* — Trevor Love
(74) *Attorney, Agent, or Firm* — Robert C. Netter, Jr.; Dann, Dorfman, Herrell & Skillman

(57) ABSTRACT

Nanofiber structures are provided along with methods of production and methods of use.

24 Claims, 7 Drawing Sheets

(51) Int. Cl.
 A61K 31/7068 (2006.01)
 A61K 9/00 (2006.01)
 A61K 9/70 (2006.01)
(52) U.S. Cl.
 CPC .............. *A61K 9/0092* (2013.01); *A61K 9/70* (2013.01); *A61L 2300/406* (2013.01); *A61L 2300/41* (2013.01); *A61L 2300/416* (2013.01); *A61L 2400/12* (2013.01)
(58) Field of Classification Search
 CPC ............ A61L 2400/12; A61K 31/7068; A61K 9/0092; A61K 9/70
 See application file for complete search history.

(56) References Cited

U.S. PATENT DOCUMENTS

| | | | |
|---|---|---|---|
| 2006/0002978 | A1 | 1/2006 | Shea et al. |
| 2007/0077272 | A1 | 4/2007 | Li et al. |
| 2008/0112998 | A1 | 5/2008 | Wang |
| 2011/0070151 | A1 | 3/2011 | Braithwaite et al. |
| 2011/0195123 | A1 | 8/2011 | Shemi |
| 2011/0293685 | A1 | 12/2011 | Kuo et al. |
| 2012/0040581 | A1 | 2/2012 | Kim |
| 2012/0226295 | A1 | 9/2012 | Jabbari |
| 2013/0095167 | A1* | 4/2013 | Warnke ................ A61K 9/7007 424/443 |

OTHER PUBLICATIONS

Nazarov, R., et al., "Porous 3-D scaffolds from regenerated silk fibroin" Biomacromolecules (2004) 5(3):718-26.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension by a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

MA, B., et al., "Rational design of nanofiber scaffolds for orthopedic tissue repair and regeneration" Nanomedicine (2013) 8(9):1459-81.

Chen, S., et al.,. "Recent advances in electrospun nanofibers for wound healing" Nanomedicine (Lond.) (2017) 12(11):1335-1352.

Xie, J., et al., "The differentiation of embryonic stem cells seeded on electrospun nanofibers into neural lineages" Biomaterials (2009) 30(3):354-362.

Xie, J, et al., "Controlled biomineralization of electrospun poly($\varepsilon$-caprolactone) fibers for enhancing their mechanical properties" Acta Biomaterialia (2013) 9(3):5698-5707.

Joshi, M.K., et al., "Multi-layered macroporous three-dimensional nanofibrous scaffold via a novel gas foaming technique" Chem. Engr. J. (2015) 275:79-88.

Pok, S., et al., "A multilayered scaffold of a chitosan and gelatin hydrogel supported by a PCL core for cardiac tissue engineering" Acta Biomater. (2013) 9(3):5630-5642.

Zhao, Y., et al., "Preparation of Nanofibers with Renewable Polymers and Their Application in Wound Dressing" Intl. J. Polmer Sci. (2016) 2016:4672839.

* cited by examiner

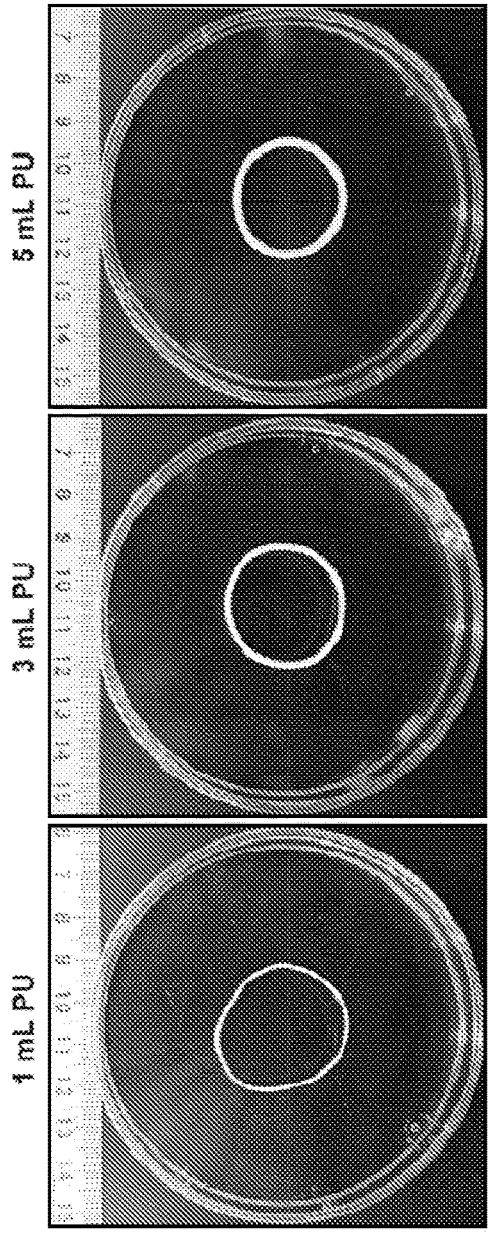
Fig. 4A
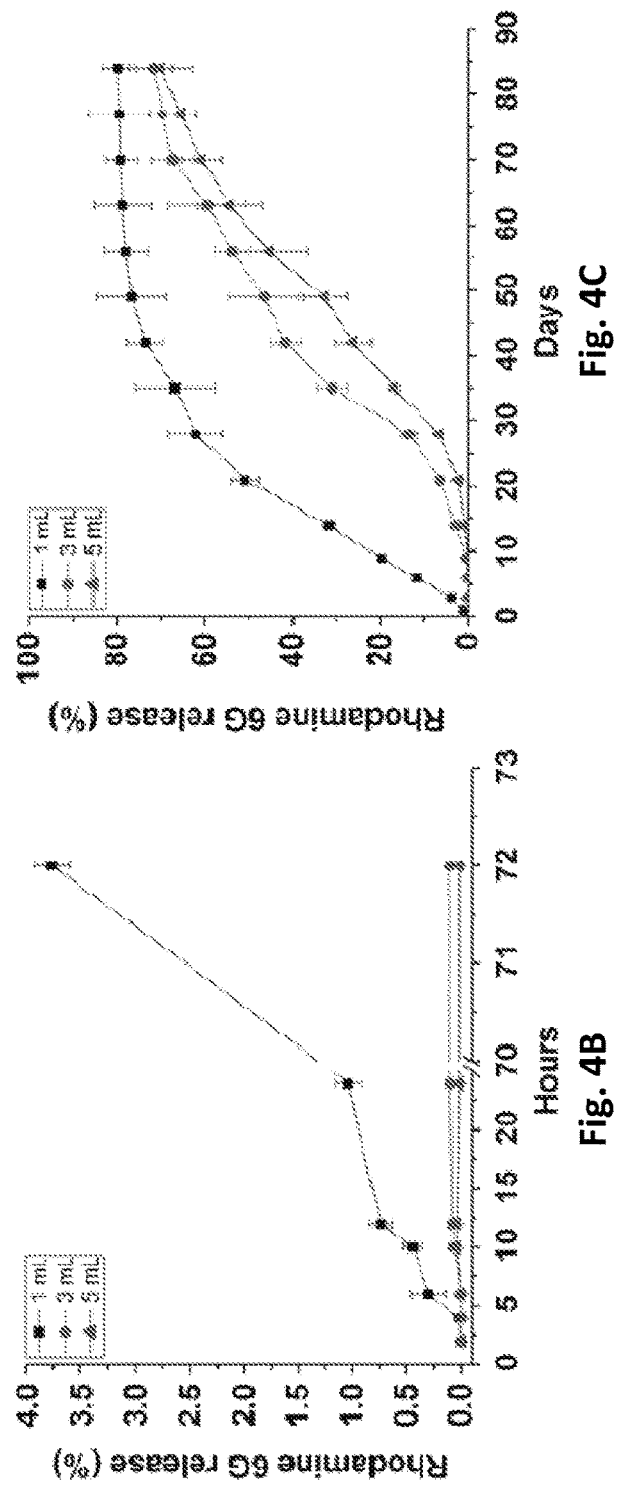
Fig. 4B
Fig. 4C

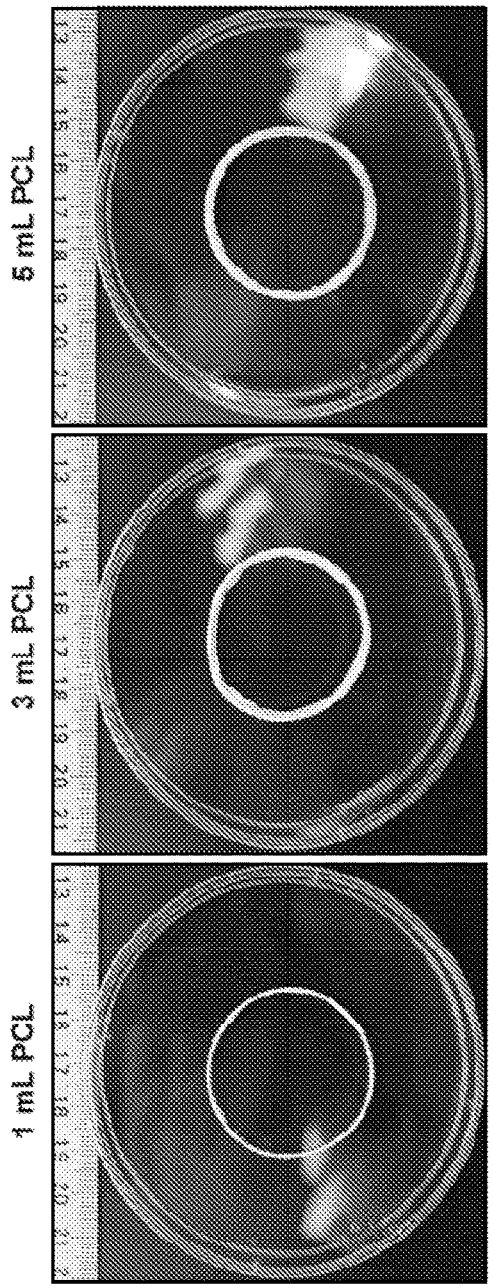
Fig. 5A
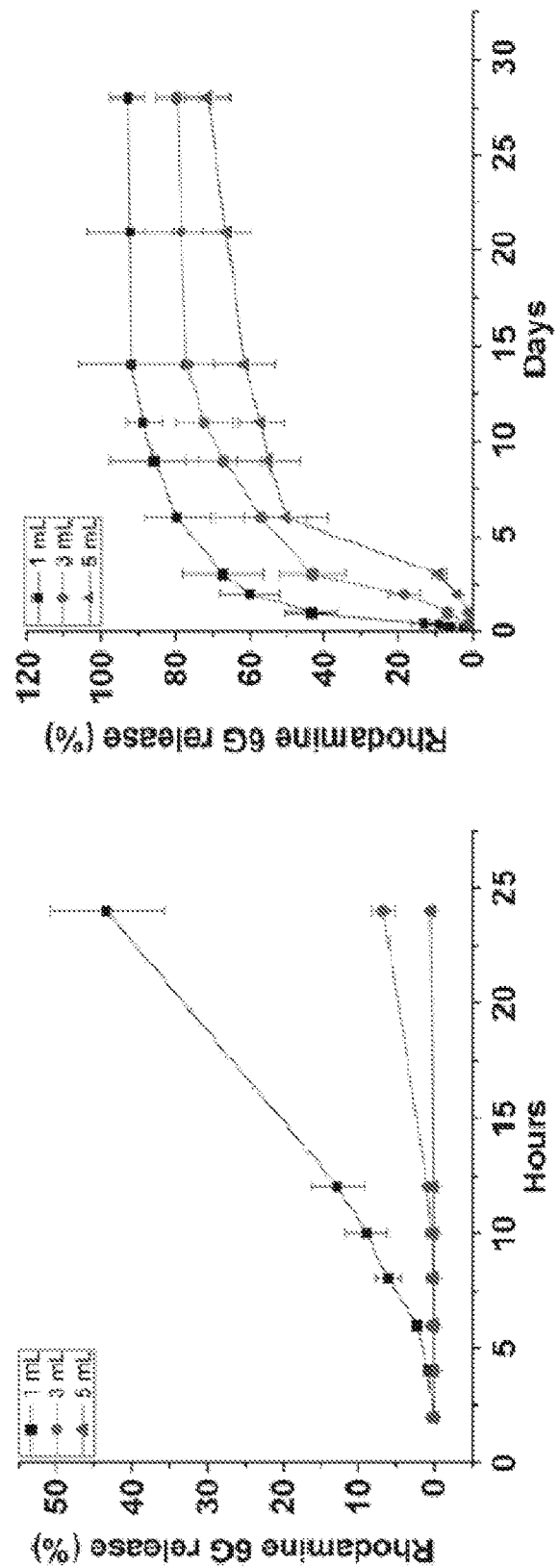
Fig. 5B
Fig. 5C

RING AND TUBULAR STRUCTURES AND METHODS OF SYNTHESIS AND USE THEREOF

This application is a § 371 application of PCT/US2017/043233, filed Jul. 21, 2017, which claims priority under 35 U.S.C. § 119(e) to U.S. Provisional Patent Application No. 62/365,023, filed Jul. 21, 2016. The foregoing applications are incorporated by reference herein.

This invention was made with government support under Grant Nos. R01 GM123081 and P20 GM103480 awarded by the National Institutes of Health (NIH). The government has certain rights in the invention.

FIELD OF THE INVENTION

This application relates to the fields of nanofiber structures. More specifically, this invention provides ring and tubular nanofiber structures, methods of making the structures, and methods of using the structures.

BACKGROUND OF THE INVENTION

Several publications and patent documents are cited throughout the specification in order to describe the state of the art to which this invention pertains. Each of these citations is incorporated herein by reference as though set forth in full.

The delivery of drugs to a target tissue can be impaired by the local environment where the drug is delivered. For example, the efficacy of chemotherapy for pancreatic cancer is impaired by a unique desmoplastic response (Olive et al., (2009) Science 324:1457-1461). Pancreatic tumors have a dense desmoplastic stroma with fibrotic connective tissue that surrounds the tumor and may account for >80% of tumor volume (Erkan et al. (2010) Exp. Oncol. 32:128-131). This leads to a microenvironment with low blood perfusion and hypoxia, serving as a barrier to diminish the delivery of anticancer drugs (Neesse et al. (2011) Gut 60:861-868). In addition, local recurrence and hepatic metastasis are still the major cause of death of patients who have undergone resection for pancreatic cancer. This is due, at least in part, because surgical wounds induce inflammation and regeneration of tissue with an increased level of cytokines favorable for tumor recurrence and metastasis (Manabe et al. (2004) J. Controlled Rel., 100:317-330). Accordingly, improved drug delivery devices capable of overcoming local barriers such as those seen with pancreatic cancer are desired (Byrne et al. (2016) Proc. Natl. Acad. Sci., 113:2200-2205; Yi et al. (2016) J. Controlled Rel. 238:231-241).

SUMMARY OF THE INVENTION

In accordance with the present invention, nanofiber structures such as rings and tubes are provided. The nanofiber structures comprise at least one rolled or spiral nanofiber membrane and at least one compound (e.g., drug or therapeutic agent). The nanofiber membranes may comprise electrospun nanofibers. In a particular embodiment, the nanofiber structure comprises at least two different compounds. The different compounds may each be distributed evenly throughout the nanofiber structure or localized to particular or distinct areas within the nanofiber structure. In a particular embodiment, the nanofiber structure comprises a first compound and a second compound, wherein in a cross-sectional view of the nanofiber structure (e.g., ring), the first compound is located towards (within) the core of the nanofiber structure and the second compound is located towards the surface of the nanofiber structure. In a particular embodiment, the nanofibers comprise hydrophobic polymers such as polycaprolactone. In a particular embodiment, the compound is hydrophilic. In a particular embodiment, the compound is a small molecule. In a particular embodiment, the compound is a therapeutic agent.

In accordance with another aspect of the instant invention, methods for producing the nanofiber structures of the instant invention are provided. In a particular embodiment, the method comprises electrospinning nanofibers onto a rotating cylindrical substrate to synthesize a nanofiber membrane, adding at least one compound to the nanofiber membrane, thereby generating a loaded nanofiber membrane, and rolling or folding the loaded nanofiber membrane to generate a nanofiber structure (e.g., ring). The addition of the compound to the nanofiber membrane may occur during the formation of the nanofiber membrane and/or after the nanofiber membrane has formed. The compounds may each be distributed evenly throughout the nanofiber membrane or localized to particular or distinct areas within the nanofiber membrane. In a particular embodiment, more than one nanofiber membrane is synthesized and rolled or folded into a single nanofiber structure.

In accordance with another aspect of the instant invention, methods of treating a disease or disorder in a subject in need thereof are provided. The method comprises administering (e.g., implanting) a nanofiber structure of the instant invention to the subject. In a particular embodiment, the disease or disorder is cancer such as pancreatic cancer and the compound of the nanofiber structure is an anticancer agent such as gemcitabine.

In accordance with another aspect of the instant invention, methods for delivering (e.g., sequentially) at least two compounds to a subject are provided. The method comprises administering (e.g., implanting) a nanofiber structure of the instant invention to the subject. In a particular embodiment, the compounds are delivered to the subject at different times via different release times from the (implanted) nanofiber structure. In a particular embodiment, at least one compound is located towards or within the core of a cross-section of the nanofiber structure (e.g., ring) for delayed or later delivery of the compound to the subject and at least one compound is located towards the surface of a cross-section of the nanofiber structure (e.g., ring) for early or rapid delivery of the compound to the subject.

BRIEF DESCRIPTION OF THE DRAWINGS

FIG. 3A provides photographs of polyurethane (PU) nanofiber membranes (top left) and PU rings (top right) and scanning electron microscope (SEM) images of the surface (bottom left) and the cross section of nanofiber rings (bottom right). FIG. 3B provides a graph of the in vitro release profiles of rhodamine 6G from PU nanofiber membranes and PU nanofiber rings.

FIG. 4A provides photographs of PU nanofiber rings of different thicknesses based on the amount (1 ml, 3 ml, or 5 ml) of PU used during electrospinning. FIG. 4B provides a graph of the in vitro release profiles of rhodamine 6G from PU nanofiber rings of different thicknesses over 72 hours. FIG. 4C provides a graph of the in vitro release profiles of rhodamine 6G from PU nanofiber rings of different thicknesses over 90 days.

FIG. 5A provides photographs of PCL nanofiber rings of different thicknesses based on the amount (1 ml, 3 ml, or 5 ml) of PCL used during electrospinning. FIG. 5B provides a graph of the in vitro release profiles of rhodamine 6G from PCL nanofiber rings of different thicknesses over 24 hours. FIG. 5C provides a graph of the in vitro release profiles of rhodamine 6G from PCL nanofiber rings of different thicknesses over 28 days.

DETAILED DESCRIPTION OF THE INVENTION

Figure 1:
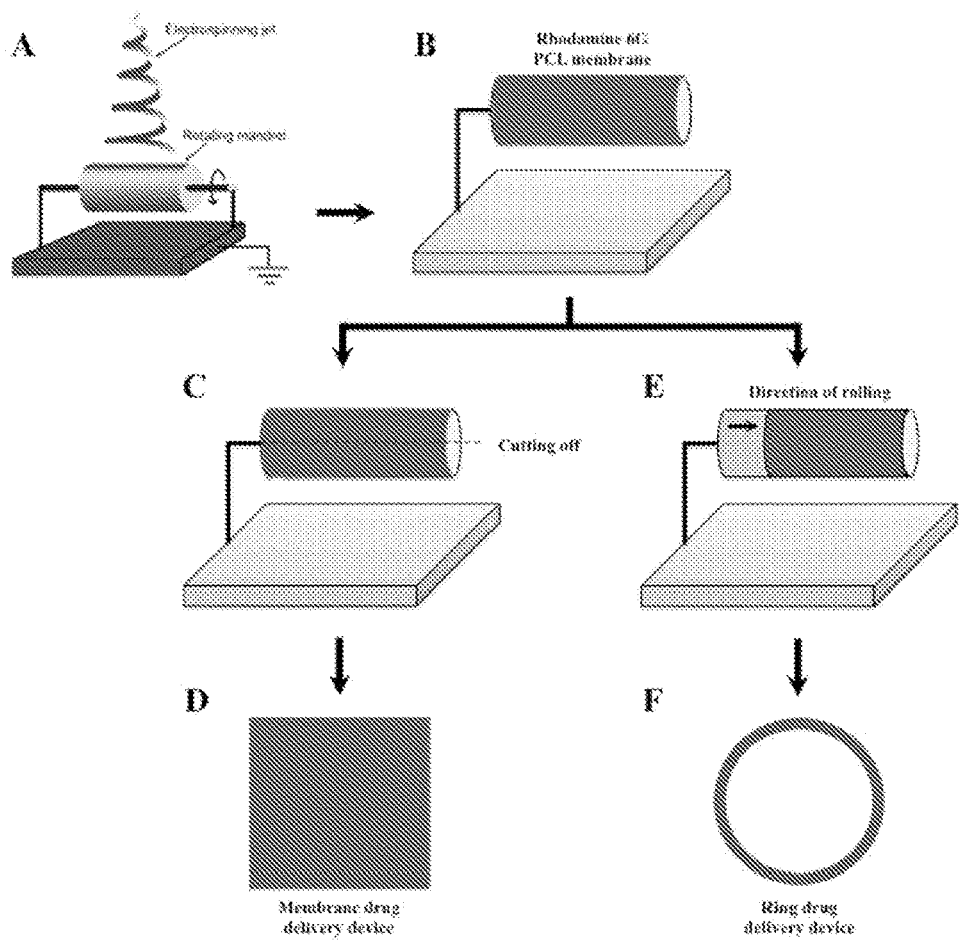
FIG. 1 provides two schematics for the fabrication of a nanofiber ring device. In Schematic 1, nanofiber membranes are electrospun on a rotating drum (A) with drug to synthesize a tubular nanofiber structure (B). The tubular nanofiber structure may be cut (C) to produce a traditional nanofiber membrane drug delivery device (D). Alternatively, the tubular nanofiber structure may be rolled (E) to create a nanofiber ring drug delivery device (F). In Schematic 2, drug loaded nanofiber tubular membranes (A) may be rolled (B) to create a nanofiber ring drug delivery device (C). A second nanofiber membrane is then electrospun on the rotating drum with a second drug (D). The first nanofiber ring drug delivery device is then used to roll the drug loaded second nanofiber membrane (E) to produce a nanofiber ring drug delivery device (F). A cross-section of the final nanofiber ring drug delivery device shows the first drug within the core and a second drug in the shell or outer layers (G).
Figure 1:
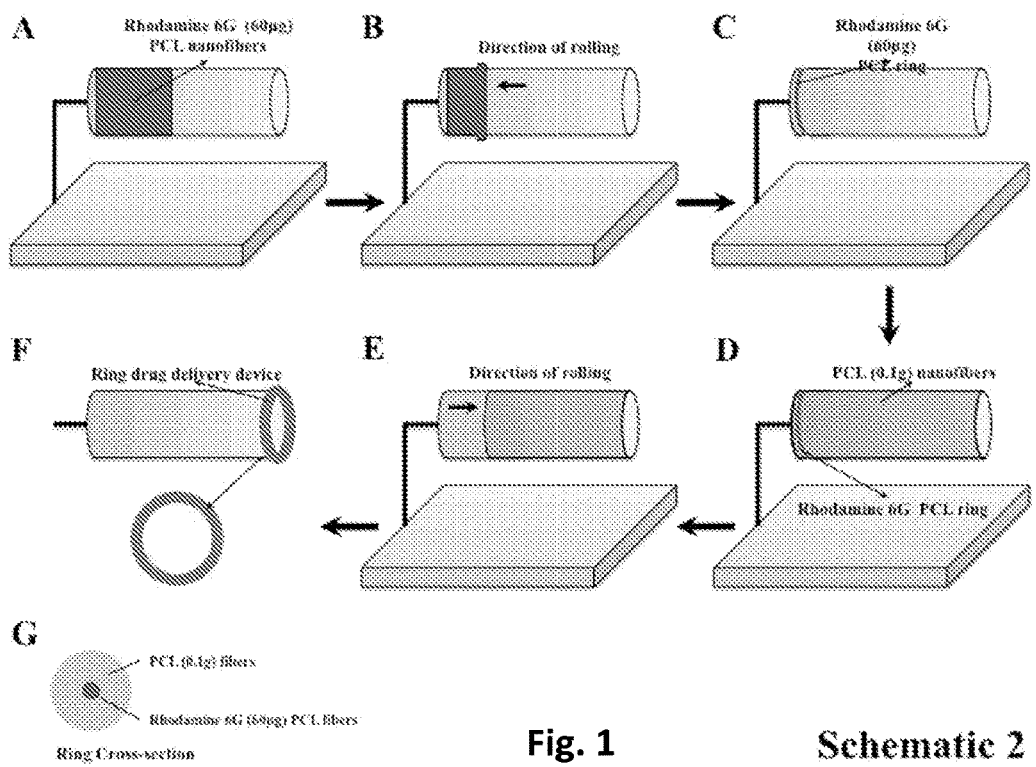

Traditional drug loaded nanofiber membranes have an initial large burst of the drug compound. Typically, this is not an ideal property for drug delivery and drug release. To improve upon current drug loaded nanofiber membranes, novel nanofiber structures (e.g., nanofiber ring or tube) structure is provided herein. The nanofiber structures of the instant invention provide improved sustained release of loaded drugs. Furthermore, the nanofiber structures of the instant invention can be designed to carry more than one drug. The nanofiber structures of the instant invention can be tailored based on the drug(s) being loaded and the disease being treated to have optimal release kinetics. The nanofiber structures of the instant invention can be designed to allow for different types of drug release including but not limited to long-term sustained release, delayed release, tagged release, sequential release of multiple drugs, and parallel release of multiple drugs.

In accordance with the instant invention, methods for producing a nanofiber structure are provided. In a particular embodiment, the method comprises rolling or folding a nanofiber membrane comprising at least one compound to form a nanofiber ring. In a particular embodiment, the method comprises electrospinning a polymer onto a rotating cylinder substrate (e.g., a mandrel, drum, or spindle) to form a nanofiber membrane, adding at least one compound to the nanofiber membrane (e.g., the compound(s) may be added as the nanofiber membrane is formed (e.g., during the electrospinning process) or after the nanofiber membrane is formed), and rolling or folding the nanofiber membrane on the cylinder substrate to form the nanofiber ring. The at least one compound(s) may be added evenly over the nanofiber membrane or may be added in distinct or overlapping areas of the nanofiber membrane. For example, compounds to be released more quickly from the nanofiber ring should be placed towards the opposite end of the nanofiber membrane from which rolling or folding begins. Similarly, compounds to have a delayed release from the nanofiber ring should be placed towards the end of the nanofiber membrane from which rolling or folding begins. In a particular embodiment, the method further comprises synthesizing another nanofiber membrane by electrospinning and rolling or folding the formed nanofiber ring over the newly synthesized nanofiber membrane. More than one additional nanofiber membrane may be added to the nanofiber ring. Each nanofiber membrane within the nanofiber ring may be loaded with one or more compounds (e.g., drugs).

In a particular embodiment, the nanofiber structure is a ring, particularly a ring of one or more rolled or spiral nanofiber membranes. While the application generally describes the structure of the nanofiber structure as a ring, the instant application encompasses nanofiber structures that are tubes. For example, the nanofiber ring structure of the instant invention may be cut to yield a nanofiber tube structure. The nanofiber tubes can also be formed directly by folding or rolling the nanofiber membrane(s). The ends of the nanofiber tube structure may be physically capped (e.g., clamped).

In a particular embodiment, the nanofiber structure of the instant invention comprises a plurality of nanofibers (e.g., uniaxially-aligned, random, entangled, and/or electrospun)). While the application generally describes nanofiber structures and the synthesis and use thereof, the instant invention also encompasses microfiber structures and the synthesis and use thereof. Generally, nanofibers are fibers having a diameter less than about 1 (e.g., average diameter) and microfibers are fibers having a diameter greater than about 1 (e.g., average diameter).

In a particular embodiment, the nanofibers are electrospun (i.e., the nanofibers are synthesized using electrospinning). The term "electrospinning" refers to the production of fibers (i.e., electrospun fibers), particularly nanofibers, from a solution or melt using interactions between fluid dynamics and charged surfaces (e.g., by streaming a solution or melt through an orifice in response to an electric or magnetic field). Electrospun nanofibers are usually deposited on a substrate to form a nanofiber mat. In a particular embodiment, the nanofibers of the instant invention are electrospun onto a curved, particularly a tubular substrate. The substrate upon which the electrospun nanofibers are deposited may be rotating (e.g., so as to synthesize a tubular nanofiber structure). Alternatively, the nanofiber dispensing unit may rotate around the substrate (e.g., so as to synthesize a tubular nanofiber structure).

The nanofibers of the instant invention may comprise any polymer. In a particular embodiment, the polymer is biocompatible. The polymer may be biodegradable or non-biodegradable. The polymer may by hydrophobic, hydrophilic, or amphiphilic. In a particular embodiment, the polymer is hydrophobic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyper-branched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini. In a particular embodiment, at least one surfactant may be added to polymer solution and/or added during nanofiber formation (e.g., to enhance stability).

Examples of hydrophobic polymers include, without limitation: polyvinyl alcohol (PVA), poly(hydroxyethyl methacrylate), polymethacrylate, poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly (tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: poly(glycerol monosterate-co-ε-caprolactone, polyvinylpyrrolidone (PVP), poly(ethylene glycol) and poly (ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO.

Amphiphilic copolymers may comprise a hydrophilic polymer (e.g., segment) and a hydrophobic polymer (e.g., segment) from those listed above (e.g., gelatin/PVA, PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen (e.g., collagen type I, II, and/or III), elastin, hyaluronic acid, cellulose, silk, silk fibroin, phospholipids (Lecithin), fibrinogen, hemoglobin, fibrous calf thymus Na-DNA, M13 viruses), synthetic polymers (e.g., PLGA, PLA, PCL, PHBV, PDO, PGA, poly[(L-lactide)-co-(e-caprolactone) (PLCL), poly[(L-lactide)-co-(D-lactide)] (PLLA-DLA), PEUU, cellulose acetate, PEG-b-PLA, poly[ethylene-co-(vinyl alcohol)] (EVOH), PVA, PEO, PVP, nylon), blended (e.g., PLA/PCL, gelatin/PVA, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA).

In a particular embodiment, the polymer is selected from the group consisting of: polymethacrylate, polyvinylphenol, polyvinylchloride, cellulose, polyvinyl alcohol, polyacrylamide, poly(lactic-co-glycolic acid) (PLGA), collagen, polycaprolactone, polyurethanes, polyvinyl fluoride, polyamide, silk, nylon, polybenzimidazole, polycarbonate, polyacrylonitrile, polylactic acid, polyethylene-co-vinyl acetate, polyethylene oxide (polyethylene glycol), polyaniline, polystyrene, polyvinylcarbazole, polyethylene terephthalate, polyacrylic acid-polypyrene methanol, poly(2-hydroxyethyl methacrylate), polyether imide, poly(ethylene-co-vinyl alcohol), polyacrylnitrile, polyvinylpyrrolidone (PVP), poly meta-phenylene isophthalamide, and combinations of two or more polymers. In a particular embodiment, the polymer is polycaprolactone (PCL). In a particular embodiment, the polymer is polyurethane (PU).

As noted hereinabove, the nanofiber ring structure of the instant invention may comprise more than one nanofiber membrane that is rolled or folded into the final nanofiber ring structure. For example, the nanofiber ring structure may comprise 1, 2, 3, 4, 5, 6, 7, 8, 9, 10 or more nanofiber membranes. Each nanofiber membrane of the nanofiber ring structure may comprise a polymer independently selected from those set forth above. In a particular embodiment, the nanofiber membranes are all synthesized from different polymers. In a particular embodiment, each nanofiber membrane comprises the same polymer. In a particular embodiment, each of the nanofiber membranes comprises a different loaded compound.

The nanofiber structures of the instant invention may comprise (e.g., be loaded) one or more compounds. For example, the nanofiber ring may comprise 1, 2, 3, 4, 5, 6, 7, 8, 9, 10 or more different compounds. In a particular embodiment, the compound is a therapeutic agent. The compounds may be hydrophobic or hydrophilic. In a particular embodiment, the compound is hydrophilic. The compound may be any natural or synthetic chemical compound (e.g., small molecule compounds), organic or inorganic compounds and molecules, biological macromolecules (e.g., saccharides, lipids, antibodies, peptides, proteins, polypeptides and nucleic acid molecules (e.g., those encoding a protein)), inhibitory nucleic acid molecules (e.g., antisense, shRNA, miRNA, or siRNA), and drugs (e.g., an FDA approved drug). Examples of compounds or therapeutic agents include, without limitation: anti-inflammatory drugs, anti-cancer drugs (e.g., cancer immunotherapy, CCL21 (Lin et al. Cancers (2014) 6(2):1098-1110), chemotherapeutics), immunotherapy drugs, antimicrobial drugs (e.g., antibiotics, antibacterials, antivirals, and antifungals), tissue regeneration activators and/or promoters (e.g., epidermal growth factor (EGF), erythropoietin (EPO)), hormones, cytokines, contraceptive drugs, and anti-pain drugs (e.g., analgesics such as opioid analgesics).

As used herein, the term "antibiotic" refers to antimicrobial agents for use in human therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, an "anti-inflammatory agent" refers to compounds for the treatment of an inflammatory disease or the symptoms associated therewith. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

Chemotherapeutic agents are compounds that exhibit anticancer activity and/or are detrimental to a cancer cell (e.g., a toxin). Suitable chemotherapeutic agents include, but are not limited to: toxins (e.g., saporin, ricin, abrin, ethidium bromide, diptheria toxin, *Pseudomonas* exotoxin); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin, oxaliplatin, and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, irinotecan, and teniposide); DNA minor groove binding agents (e.g., plicamydin); nucleoside analogs (e.g., gemcitabine); tyrosine kinase inhibitors (e.g., erlotinib); thymidylate synthase inhibitor (e.g., folinic acid); antimetabolites (e.g., folate antagonists such as methotrexate and trimetrexate; pyrimidine antagonists such as fluorouracil (e.g., 5-fluorouracil), fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); HSP90 inhibitors (e.g., 17-AAG); and antihormonal antigens (e.g., tamoxifen, antiandrogen agents such as flutamide; and antiadrenal agents such as mitotane and aminoglutethimide).

In a particular embodiment, at least one compound of the nanofiber structure is chemotherapeutic agent. In a particular embodiment, the chemotherapeutic agent is effective against pancreatic cancer. In a particular embodiment, the chemotherapeutic agent is selected from the group consisting of gemcitabine, erlotinib, 5-fluorouracil, paclitaxel (e.g., albumin-bound paclitaxel), folinic acid, irinotecan, and oxaliplatin. In a particular embodiment, the chemotherapeutic agent is gemcitabine. In a particular embodiment, the chemotherapeutic agent is gemcitabine along with an agent selected from the group consisting of erlotinib, 5-fluorouracil, paclitaxel (e.g., albumin-bound paclitaxel), folinic acid, irinotecan, and oxaliplatin.

The compounds may be added to the nanofiber structure in a variety of ways. For example, the compounds may be added before, during, and/or after the electrospinning process. In a particular embodiment, the compound(s) may be added during the electrospinning process. For example, the compound(s) may be in solution with the polymer as the polymer is electrospun onto a substrate. In a particular embodiment, the compound(s) is added to the nanofibers during the electrospinning process. In a particular embodiment, the compound(s) is added to the nanofibers after the electrospinning process. For example, the nanofibers may be synthesized and then the compound(s) added to the nanofiber structure prior to manipulation of the nanofiber structure (e.g., prior to rolling and or folding the nanofiber structure). The compounds may be added at different/distinct locations of the nanofiber structure. For example, compounds to be released later (e.g., have a delayed release) maybe placed towards the location of manipulation (e.g., rolling and/or folding) of the nanofiber structure such that the compound will be located towards the core of the final nanofiber structure. As an example, if a single nanofiber membrane is used, the compound intended for delayed release may be placed within the middle half or within the middle (center) 50%, 40%, 30%, 20%, 10%, or less by cross-sectional area. As an another example, if multiple nanofiber membranes are used, the compound intended for delayed release may be placed within one of the nanofiber membranes towards or at the core of the cross-sectional view. Conversely, compounds to be released earlier (e.g., have a quick release) may be placed towards the opposite end of the manipulation (e.g., rolling and/or folding) of the nanofiber structure such that the compound will be located towards the surface of the final nanofiber structure. As an example, if a single nanofiber membrane is used, the compound intended for early or quick release may be placed outside the middle half or outside the middle (center) 50%, 60%, 70%, 80%, 90%, or more by cross-sectional area. As an another example, if multiple nanofiber membranes are used, the compound intended for quick or early release may be placed within one of the nanofiber membranes towards or at the surface of the cross-sectional view.

The following are examples of methods for fabricating and testing nanofiber ring devices of the instant invention. Briefly, a polymer solution for electrospinning can be made comprising at least one polymer (e.g., a biodegradable polymer such as polycaprolactone (PCL) or a non-biodegradable polymer such as polyurethane (PU)) and, optionally, at least one compound (e.g., a therapeutic agent or drug). The polymer may be present at about 1% to about 60%, about 10% to about 40%, about 10% to about 30%, about 15% to about 25%, or about 20% weight/volume in a solvent (e.g., a mixture of dichloromethane (DCM) and dimethylformamide (DMF); e.g., at a volume ratio of about 4:1). Polymer solutions may be pumped (e.g., at a flow rate of about 0.05 mL/h to about 5 mL/h, about 0.1 mL/h to about 3 mL/h, or about 0.5 mL/h) using a syringe pump while applying a electric potential (e.g., about 0.5 kV to about 100 kV, about 1 kV to about 50 kV, about 5 kV to about 25 kV, or about 12 kV) between the spinneret (e.g., a needle such as a 22-gauge needle) and a grounded rotating mandrel/drum (e.g., located about 1 cm to about 50 cm, about 3 cm to about 40 cm, about 5 cm to about 25 cm, or about 12 cm from the spinneret). The nanofiber membranes deposited on the drum may then be rolled up or folded up to form a ring. The morphology of the nanofiber rings may be examined using scanning electron microscope (SEM) and the secondary structure of the nanofiber rings may be characterized using a transmission electron microscope (TEM).

Compounds (e.g., drugs) may be encapsulated within the nanofibers using various protocols (Xie et al. (2012) Acta Biomater., 8:811-819; Xie et al. (2008) J. Colloid Interface Sci., 317:469-476). Water soluble compounds may be added using a co-axial electrospinning technique to fabricate core-sheath nanofibers by encapsulating the water soluble compound in the core for prolonged release. Briefly, the water soluble compound may be dissolved in water to form the core solution. PCL or PU may be dissolved in a mixture of DCM and DMF to form the shell solution. The drug loading can be readily controlled by varying the concentration of the core solution and the ratio of flow rates between the core solution and the shell solution. The layer thickness may also be controlled by the nanofiber deposition time. The number of layers may be controlled by the length of the rotating drum/mandrel. All of these parameters can be used to tailor the release profiles of encapsulated compounds. The morphology of the compound-loaded nanofiber rings may be examined using scanning electron microscope (SEM) and the secondary structure of the nanofiber rings may be characterized using a transmission electron microscope (TEM). Differential scanning calorimetry (DSC) may also be used to determine the physical status (e.g., amorphous, crystalline) of the encapsulated compounds.

The multiple-layer structure of nanofiber-based rings allows the long-term sustained release of compounds in different layers (Falde et al. (2015) J. Controlled Rel., 214:23-29; Liu et al. (2015) Nanomedicine: NBM, 11:1047-1056). The water penetration from the outer layer to the inner layer may be examined using fluorescence microscope and micro-CT (Falde et al. (2015) J. Controlled Rel., 214: 23-29). The actual compound loading in nanofiber rings may be determined by high performance liquid chromatography (HPLC) (Khare et al. (2016) Eur. J. Pharm. Sci., 92:183-193). The amount of compound loaded can be greater than 1 mg per ring device. Briefly, weighted nanofiber rings may be dissolved in acetonitrile (e.g., 400 µl) and the compound may be extracted by adding water (e.g., 600 µl). The samples may be analyzed using HPLC (e.g., equipped with a RP 18 column with a photodiode array (PDS) detector). A desired solvent (e.g., acetonitrile and 0.02 M ammonium acetate buffer (1:1)) may be used as mobile phase (e.g., with a flow rate of 0.5 ml/minute). The presence of the compounds may be measured by the detection wavelength of the compound (e.g., 268 nm for gemcitabine). To quantify in vitro release of the compounds, the nanofiber-based rings may be incubated in aqueous solution such as phosphate buffer saline (PBS) at 37° C. At predetermined time intervals, the supernatant may be collected for HPLC analyses.

The in vitro efficacy of loaded nanofiber rings can be tested using standard methods. For example, the efficacy of gemcitabine loaded nanofiber-based rings to induce apoptosis in the human (e.g., Capanl, CD18/HPAF) and/or mouse (e.g., KCT961, KCT960) pancreatic cancer cell lines may be tested (Macha et al. (2013) Cancer Lett., 341:166-177). Notably, hypoxia is a characteristic feature of pancreatic cancer and is responsible for chemotherapeutic resistance. Therefore, apoptosis experiments under hypoxic conditions may be performed. Briefly, pancreatic cancer cell lines may be cultured (e.g., in 10% DMEM media) with and without hypoxia conditions using a hypoxia chamber and/or chemically induced hypoxia conditions by using $CoCl_2$. The rings loaded with gemcitabine may be placed along with the cells and the cell viability/growth may be measured (e.g., using an MTT ((3-(4,5-dimethylthiazol-2-yl)-2,5-diphenyltetrazolium bromide)) assay) at different time points. Cell survival may be confirmed by colony forming assays (e.g., the cells may be grown in a 6-well plate and treated with the gemcitabine loaded ring device for different times and the colony formation may be analyzed). The effect of gemcitabine-loaded nanofiber ring device on cellular apoptosis may also be studied (e.g., by flow cytometry using an Annexin/propidium iodide (PI) assay).

Pancreatic cancer cells have higher levels of reactive oxygen species (ROS) that play critical role in the overall survival of the cells. Studies have demonstrated that gemcitabine modulate the levels of ROS in the pancreatic cancer cells (Ju et al. (2015) Mol. Cancer Ther., 14:788-798). Therefore, the levels of ROS production after the treatment with the gemcitabine loaded ring device may be analyzed (Tones et al. (2012) Cancer Lett., 323:29-40). This effect may also be studied under hypoxia. For example, pancreatic cancer cells may be cultured under normoxia and hypoxia in the presence of the loaded nanofiber ring and reactive oxygen species (ROS) may be measured (e.g., using ROS sensitive probes (e.g, dihydroethidium (hydroethidine; DHE), 2',7'-dichlorofluorescin (DCF), and MitoSOX™) by confocal microscopy and flow cytometry). The levels of the cellular antioxidants (e.g., superoxide dismutase (SOD), glutathione (GSH)/glutathione disulfide (GSSG)) may be also measured after the treatment. Trans-well motility and wound healing assays may also be used to measure the migration capacity of human pancreatic cancer cells in the presence of the loaded nanofiber rings under hypoxic and/or normoxic conditions (Torres et al. (2012) Cancer Lett., 323:29-40).

The in vivo efficacy of loaded nanofiber rings can be tested using standard methods. For example, the efficacy of optimized gemcitabine loaded nanofiber rings may be evaluated in animal pancreatic cancer models such as nude and syngeneic mouse pancreatic cancer models (Wang et al. (2016) Biomaterials 101:108-120; Torres et al. (2012) Cancer Lett., 323:29-40). A mouse spontaneous pancreatic ductal adenocarcinoma model may also be used (Rachagani et al. (2012) J. Hematology Oncol., 5:68; Tones et al. (2013) PLoS ONE 8:e80580). An orthotopic analysis may be performed in nude mice with a pancreatic cancer cell line (e.g., CD18/HPAF) and/or in the C57BL/6 immunocompetent animals for the mouse cell line (KCT961). For example, approximately $5 \times 10^5$ cells in 50 µl PBS with a 1:1 mix of matrigel may be implanted into the tail of the pancreas by making an incision (e.g., 1 cm) at the mid-abdomen region below the sternum with the help of a scissor without causing injury to the peritoneal wall and internal organs. Prior to surgery, the mice (e.g., 6 weeks old) may be anesthetized. The peritoneum may be cut open and with help of blunt forceps, the duodenum may be pulled out slowly and cells may be injected into the head of pancreas without causing injury and torsion. The abdomen may be closed by using a 2-layer suture with 5-0 chromic catgut and soft staple. The skin staples/sutures may be left in for at least 10-14 days post-operatively.

After the tumor is visible (e.g., using an in vivo imaging system), an incision may be made to treat with three different groups: intraperitoneal (i.p.) administration of gemcitabine, without treatment, and implantation of gemcitabine-loaded nanofiber ring device (Torres et al. (2012) Cancer Lett., 323:29-40). The small incision may be made at the mid-abdomen region below the sternum with the help of a scissor without causing injury to the peritoneal wall and internal organs. The device may be implanted/immobilized to the stomach wall with the help of the fine sutures and the abdomen may be closed by using a 2-layer suture with 5-0 chromic catgut and soft staple. The skin staples/sutures may be left in for at least 10-14 days post-operatively. The animals may be euthanized 30 days post-implantation of the gemcitabine loaded device and pancreas (tumor), lung, and liver may be harvested and fixed in buffered formalin and frozen in liquid nitrogen for further analysis (e.g., by immunohistochemistry and quantitative reverse transcription PCR (qRT-PCR)). A separate group of the animals may be followed for a survival analysis from the gemcitabine-loaded nanofiber-based ring device.

An immunohistochemistry (IHC) analysis on the orthotopic and autochthonous models may be performed as per standard protocol, including hydration, antigen retrieval, and incubation with primary and secondary antibodies, developing with DAB reagent, and counter staining by hematoxylin (Torres et al. (2012) Cancer Lett., 323:29-40). Tissues may be analyzed for cellular proliferation (Ki-67, proliferating cell nuclear antigen (PCNA)), apoptosis (terminal deoxynucleotidyl transferase dUTP nick end labeling (TUNEL) and cleaved caspase 3), CD31, CD133, CD44, and desmoplasia (e.g., Masson's trichrome). The liver, lung and other organs may be analyzed for the presence of the metastatic lesion and will also be stained for above mentioned analysis. The expression of proteins of interest may be analyzed by a pathologist and scoring may be done on the basis of composite scores calculated based on the percentage of positively stained cells (e.g., <5%=0, 5-25%=1, 26-50%=2, 51-75%=3 and 76-100%=4) and the intensity of the staining (e.g., 0, 1+, 2+, 3+). The protein lysate from the tumor may be prepared by standard protocol (e.g., RIPA buffer) and analyzed for the expression of epithelial markers, activated fibroblast, and extracellular matrix protein to evaluate the impact of sustained release of gemcitabine on the pancreatic tumor.

To avoid the drug resistance, sequential and/or simultaneous treatment with multiple drugs may result in better outcome for pancreatic cancer (Ubezio et al. (2016) Oncogarget 7:15492-15506; Conroy et al. (2011) N. Engl. J. Med., 364:1817-1825; Von Hoff et al. (2013) N. Engl. J. Med., 369:1691-1703). As explained herein, multiple drugs can be incorporated in different layers of nanofiber-based ring devices for sequential release. For example, the drugs may be loaded on the nanofiber structure at different locations prior to rolling of the nanofiber such that drugs located closest to the beginning of rolling are in the core of the structure and are the slowest to release whereas drugs located farthest from the beginning of the rolling are on the edge or surface of the structure and are the first to release. In another embodiment, multiple drugs may be incorporated or distributed evenly throughout the layers of ring devices for simultaneous release.

In accordance with the instant invention, nanofiber rings (or tubes) are provided. In a particular embodiment, the nanofiber comprises a ring of at least one rolled or spiral nanofiber membrane comprising at least one compound. In a particular embodiment, the nanofiber rings are produced by the methods of the instant invention. The nanofiber ring may be contained within a composition comprising water or a biologically and/or pharmaceutically acceptable carrier. The nanofiber ring may be a scaffold for biomedical research such as regenerative medicine or tissue model. Applications for nanofiber structures are provided in Xie et al. (Macromol. Rapid Commun. (2008) 29:1775-1792; incorporated by reference herein). In a particular embodiment, the nanofiber ring comprises or encapsulates at least one compound (e.g., a therapeutic agent, growth factor, signaling molecule, cytokine, antibiotic, etc.). In a particular embodiment, the nanofibers of the instant invention (in the methods of synthesis or the final product) are labeled or modified with at least one agent or compound (e.g., a therapeutic agent, therapeutic agent, growth factor, signaling molecule, cytokine, antibiotic, etc.), using either surface conjugation/coating and/or encapsulation (e.g., to modulate cellular responses and/or encourage tissue regeneration).

In accordance with the instant invention, methods for the inhibition, prevention, and/or treatment of a disease or disorder in a subject in need thereof are provided. For example, the nanofiber rings can be used to inhibit, prevent, and/or treat a variety of conditions including but not limited to cancer, pain, microbial infections, and inflammatory disorders. The nanofiber rings can also be used for tissue regeneration including but not limited to blood vessel growth, neural tissue regeneration and bone regeneration. In a particular embodiment, the method comprises administering at least one nanofiber ring of the instant invention (or a composition comprising at least one nanofiber ring) to the subject, wherein the nanofiber ring comprises at least one compound (e.g., therapeutic agent) for the disease or disorder to be treated). The methods may comprise the administration of one or more nanofiber rings. When more than one nanofiber ring is administered, the nanofiber rings may be administered simultaneously and/or sequentially.

In a particular embodiment, the present invention provides compositions and methods for the inhibition (e.g., reduction, slowing, etc.), prevention, and/or treatment of cancer. Cancers that may be treated using the present methods include, but are not limited to: prostate cancer, colorectal cancer, colon cancer, pancreatic cancer, cervical cancer, gastric cancer, endometrial cancer, brain cancer, liver cancer, bladder cancer, ovarian cancer, testicular cancer, head cancer, neck cancer, skin cancer (including melanoma and basal carcinoma), mesothelioma, white blood cell cancer (including lymphoma and leukemia), esophageal cancer, breast cancer, muscle cancer, connective tissue cancer, lung cancer (including small-cell lung carcinoma and non-small-cell carcinoma), adrenal gland cancer, thyroid cancer, renal cancer, bone cancer, glioblastoma, sarcoma, choriocarcinoma, cutaneous basocellular carcinoma, and testicular seminoma. In a particular embodiment, the cancer is a solid tumor. In a particular embodiment, the cancer is a pancreatic cancer. In a particular embodiment, the method comprises administering to the subject a nanofiber ring comprising more than one anticancer drug. In a particular embodiment, the nanofiber ring comprises at least one chemotherapeutic and at least one cancer immunotherapy. In a particular embodiment, the nanofiber ring comprises at least one chemotherapeutic and CCL21. In a particular embodiment, the nanofiber ring comprises CCL21 and at least one cancer immunotherapy. In a particular embodiment, the method comprises resecting the tumor (e.g., pancreatic cancer tumor) and administering the nanofiber ring comprising more than one anticancer drug (e.g., gemcitabine). In a particular embodiment, the method comprises administering the nanofiber ring comprising more than one anticancer drug and administering radiotherapy to the subject.

In a particular embodiment, the disease or disorder is associated with insufficient or improper fistula maturation and/or vain vessel growth (e.g., dialysis fistula maturation). In a particular embodiment, the method comprises administering to the subject a nanofiber ring comprising matrix metalloproteinase-1 (MMP1) located towards the surface (for quick release) and basic fibroblast growth factor (bFGF) located towards the core (for delayed release).

In a particular embodiment, the disease or disorder is associated with insufficient or improper angiogenesis (i.e., the method promotes angiogenesis). In a particular embodiment, the method comprises administering to the subject a nanofiber ring comprising vascular endothelial growth factor (VEGF), basic fibroblast growth factor (bFGF), platelet-derived growth factor (PDGF) or a combination thereof.

In a particular embodiment, the disease or disorder is associated with deficient neural (e.g., brain) tissue (i.e., the method promotes neural tissue regeneration). In a particular embodiment, the method comprises administering to the subject a nanofiber ring comprising epidermal growth factor (EGF) located towards the surface (for quick release) and erythropoietin (EPO) located towards the core (for delayed release).

In a particular embodiment, the disease or disorder is associated with deficient bone (i.e., the method promotes bone regeneration). In a particular embodiment, the method comprises administering to the subject a nanofiber ring comprising VEGF and/or bFGF (optionally located towards the surface for quick release) and bone morphogenetic protein 2 (BMP-2) (optionally located towards the core for delayed release).

In a particular embodiment, the disease or disorder is associated with a microbial infection (e.g., a bacterial infection). In a particular embodiment, the method comprises administering to the subject a nanofiber ring comprising more than one antimicrobial. In a particular embodiment, the nanofiber ring comprises at least one antimicrobial and at least one probiotic.

In accordance with another aspect of the instant invention, methods for contraception are provided. In a particular embodiment, the method comprises administering to the subject (e.g., to the uterus or vagina) a nanofiber ring comprising at least one contraceptive.

The nanofiber rings of the instant invention may be administered to a patient as a pharmaceutical preparation. The term "patient" as used herein refers to human or animal subjects. These nanofiber rings may be employed therapeutically, under the guidance of a physician.

The pharmaceutical preparation comprising the nanofiber rings of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated. Selection of a suitable pharmaceutical preparation depends upon the method of administration chosen.

Typically, the nanofiber rings of the invention will be implanted into the subject (although the nanofiber rings may also be taken orally). For example the nanofiber rings of the instant invention may be inserted into any cancerous tissue or into the surrounding area. In this instance, a pharmaceutical preparation comprises the agents dispersed in a medium that is compatible with the target tissue (e.g., cancerous tissue).

The nanofiber rings of the instant invention may be administered at appropriate intervals until the pathological symptoms are reduced or alleviated, after which the dosage may be reduced to a maintenance level, if needed. The appropriate interval in a particular case would normally depend on the condition of the patient.

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

As used herein, the term "small molecule" refers to a substance or compound that has a relatively low molecular weight (e.g., less than 4,000 atomic mass units (a.m.u. or Da), less than 2,000 Da., particularly less than 1 kDa or 800 Da). Typically, small molecules are organic, but are not proteins, polypeptides, amino acids, or nucleic acids.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

A "therapeutically effective amount" of a compound or a pharmaceutical composition refers to an amount effective to prevent, inhibit, treat, or lessen the symptoms of a particular disorder or disease. The treatment of a disease or disorder herein may refer to curing, relieving, and/or preventing the disease or disorder, the symptom of it, or the predisposition towards it.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including mammals such as humans.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

The following examples are provided to illustrate certain embodiments of the invention. They are not intended to limit the invention in any way.

Example 1

Traditionally, co-axial electrospinning can readily produce loaded electrospun nanofiber membranes. For example, PCL nanofiber membranes can be peeled from a rotating mandrel after electrospinning. In order to fabricate nanofiber ring devices, nanofibers were first deposited on the mandrel. Then, the nanofibers deposited on the mandrel were rolled up and/or folded to form a ring. FIG. 1 provides illustrations of methods for the fabrication of nanofiber rings. Compounds (e.g., therapeutic agents) can be deposited on the nanofibers before rolling up and/or folding.

Figure 2:
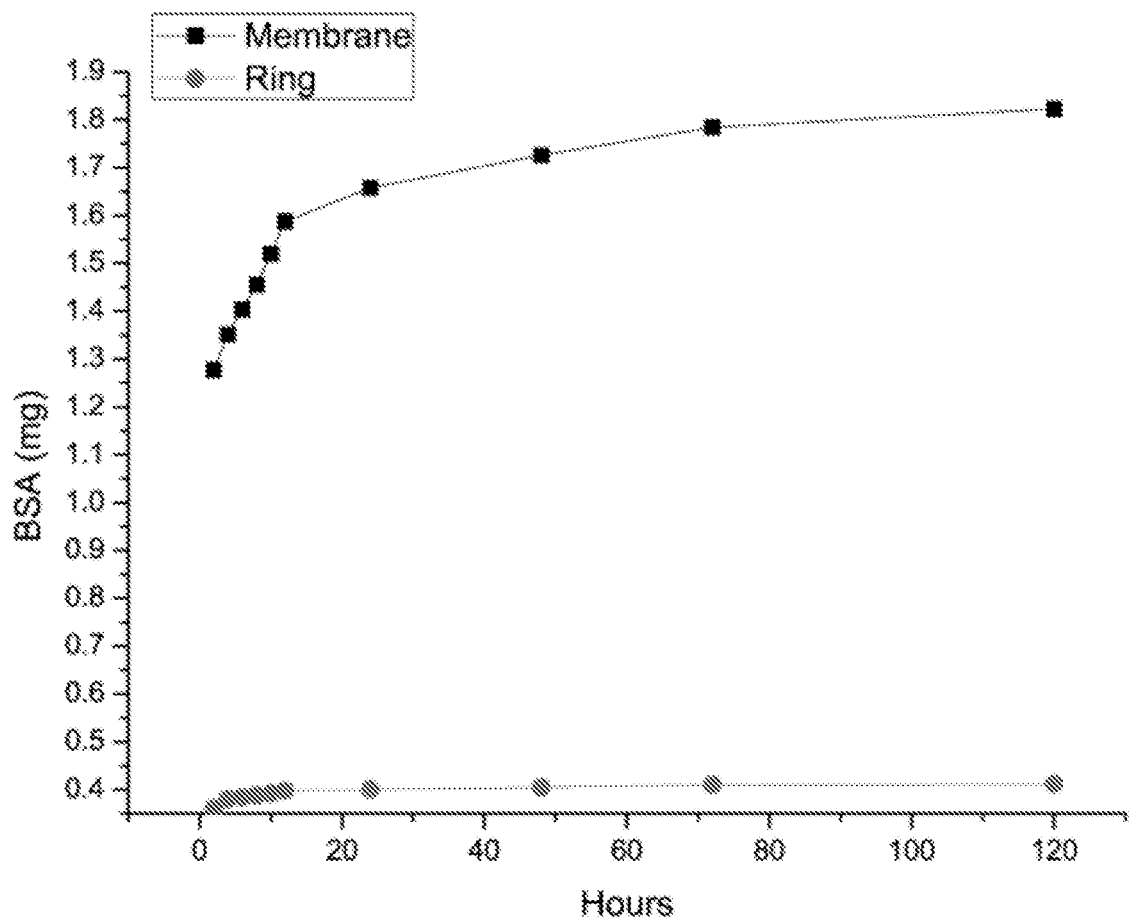
FIG. 2 provides a graph of the in vitro release profile of bovine serum albumin (BSA) from polycaprolactone (PCL) nanofiber membranes and rings.

FIG. 2 shows the in vitro release profile of BSA from traditional electrospun nanofiber membranes and the nanofiber ring devices of the instant invention. It is observed that BSA has a large initial burst at the beginning for electrospun nanofiber membranes. In stark contrast, the nanofiber ring device of the instant invention significantly inhibits the initial release of the loaded compound. Accordingly, nanofiber ring devices provide significantly longer sustained release of loaded compounds.

Example 2

Pancreatic ductal adenocarcinoma is the fourth most common cause of death from cancer in the United States, having a five-year survival rate less than 5% (Hidalgo, M. (2010) N. Engl. J. Med., 362:1605-1617; Ryan et al. (2014) N. Engl. J. Med., 371:1039-1049; Garrido-Laguna et al. (2015) Nat. Rev. Clin. Oncol., 12:319-334). Pancreatic cancer is a highly aggressive disease because of its tendency for early spreading and metastasis. Chemotherapy is a standard treatment after resection of the tumor to prevent recurrent growth and metastasis of remaining malignant cells. However, a low survival rate ranging from 8-25% has been reported for resectable pancreatic cancer patients (Fischer et al. (2012) Saudi J. Gastroenterol., 18:118-121). Hence, a novel nanofiber ring device is provided herein using electrospinning and folding/rolling in which anticancer drugs are incorporated. The nanofiber rings will provide a locally sustained delivery of drugs over a long period of time at the resection site, thereby effectively inhibiting tumor progression and metastasis.

Electrospinning is an enabling technique to incorporate different therapeutic agents, eliciting sustained release properties (Xie et al. (2006) Pharm. Res., 23:1817-1826; Jiang et al. (2015) Pharm. Res., 32:2851-2862; Xie et al. (2008) Rapid Commun. 29:1775-1792; Xie et al. (2008) J. Biomed. Mater. Res. A, 85:897-908). Compounds can be encapsulated in polymeric nanofibers during electrospinning process (Xie et al. (2006) Pharm. Res., 23:1817-1826). The duration for the release of hydrophobic molecules can last more than 2 months, which is mainly determined by the hydrophobicity of molecules. However, the release profiles of hydrophilic molecules from nanofiber matrices often exhibit a high initial burst followed by short-term gradual release (Jiang et al. (2015) Pharm. Res., 32:2851-2862). Herein, a unique nanofiber ring device is provided with multiple layers with incorporation of gemcitabine, a nucleoside analog, for local treatment of resectable pancreatic cancer as the anticancer potential of gemcitabine is compromised due to the enzymatic degradation into inactive form leading to the short half-life in systemic circulation (Khare et al. (2016) Eur. J. Pharm. Sci., 92:183-193). Without being bound by theory, the unique structure allows a long-term sustained release as it takes time for water to penetrate from the outer layer to the inner layer due to the nature (e.g., hydrophobicity) of the polymeric nanofiber matrices.

Figure 3A:
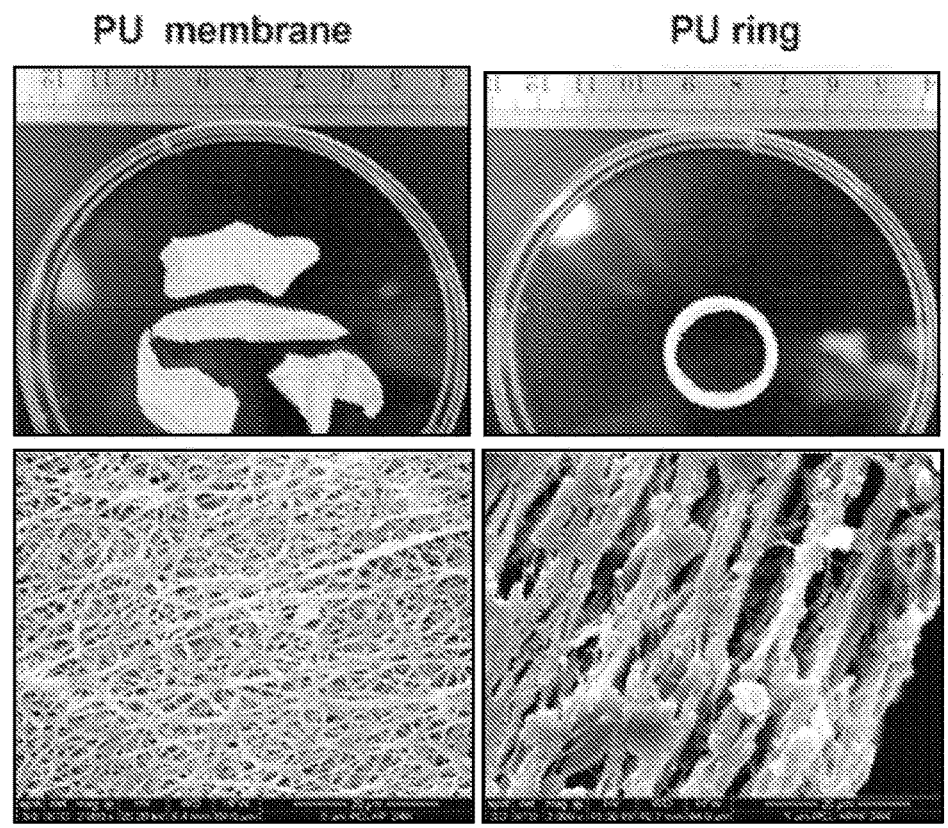
FIGS. 3A and 3B provide a comparison between nanofiber-based membranes and rings.
Figure 3B:
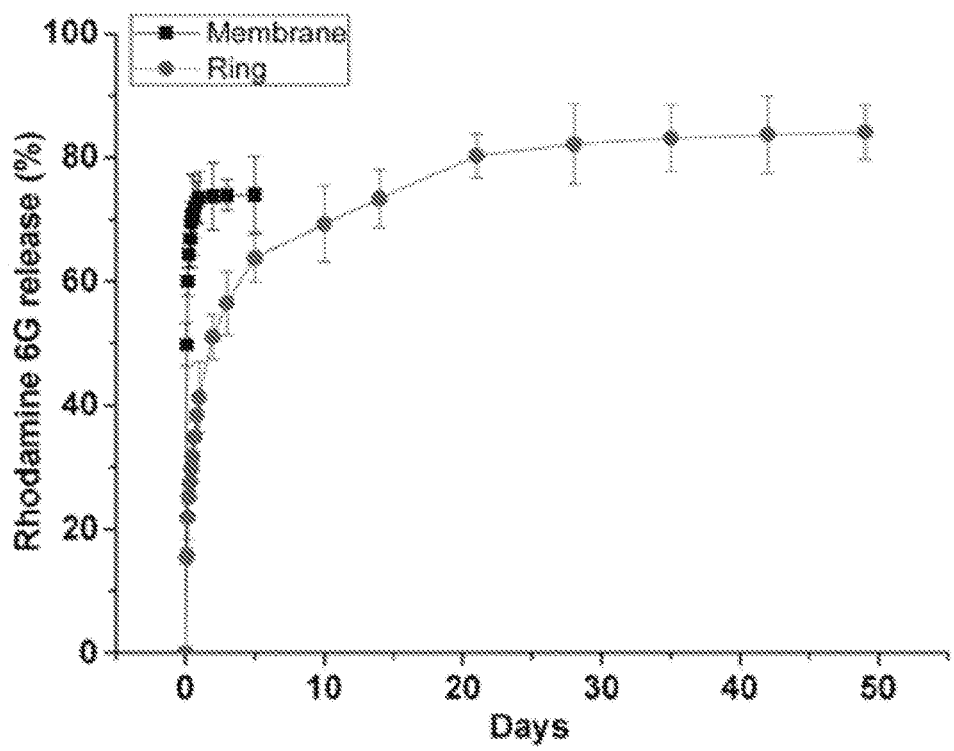
Figure 6A:
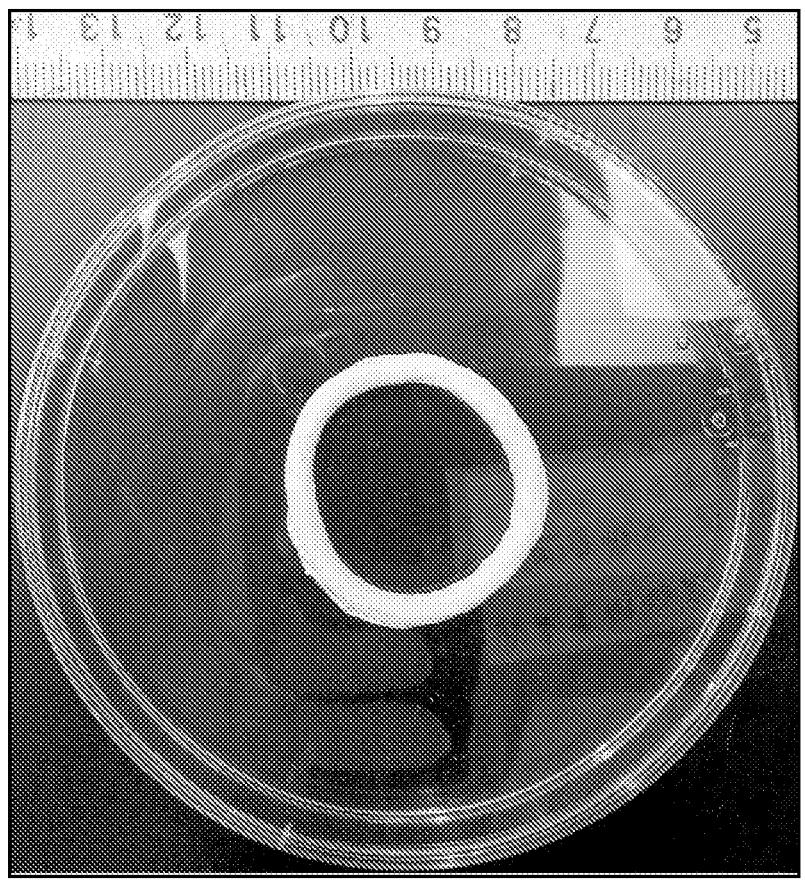
FIG. 6A provides a photograph showing a PU nanofiber ring device with BSA in the shell and rhodamine 6G in the core.
Figure 6B:
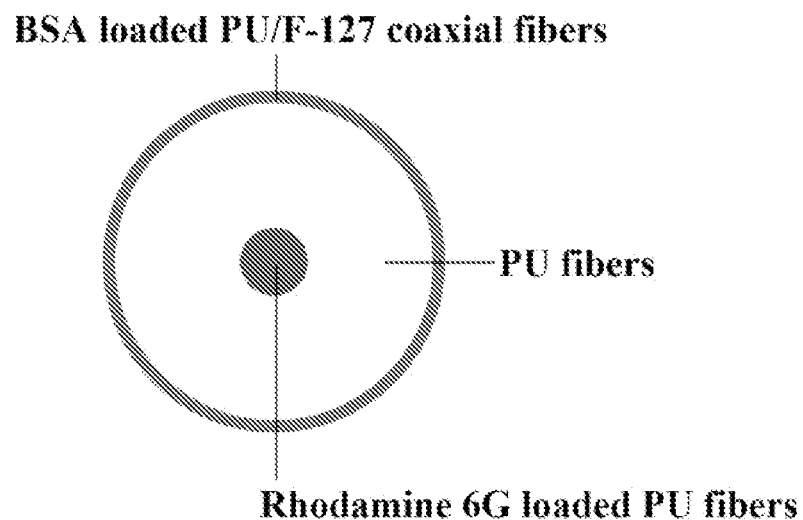
FIG. 6B provides a cross section schematic showing a nanofiber ring device with BSA in the shell and rhodamine 6G in the core.
Figure 6C:
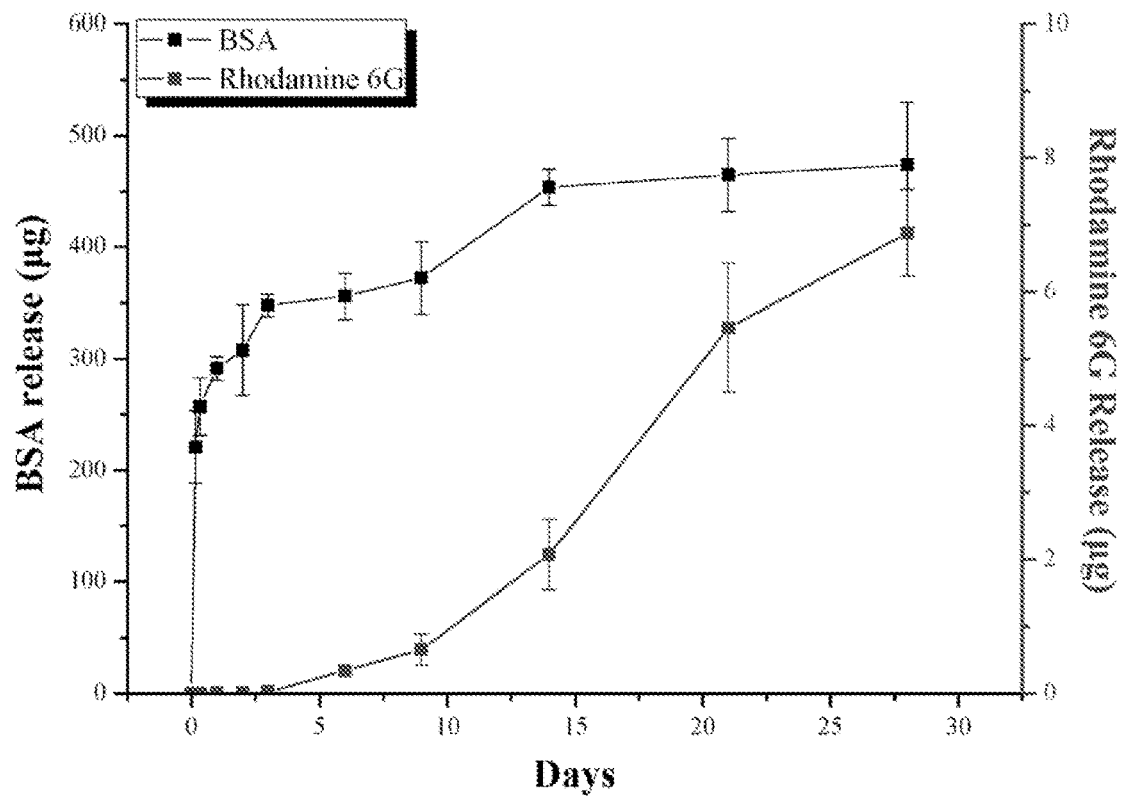
FIG. 6C provides graphs of the in vitro release profiles of BSA and rhodamine 6G with different load amounts.
Figure 6C:
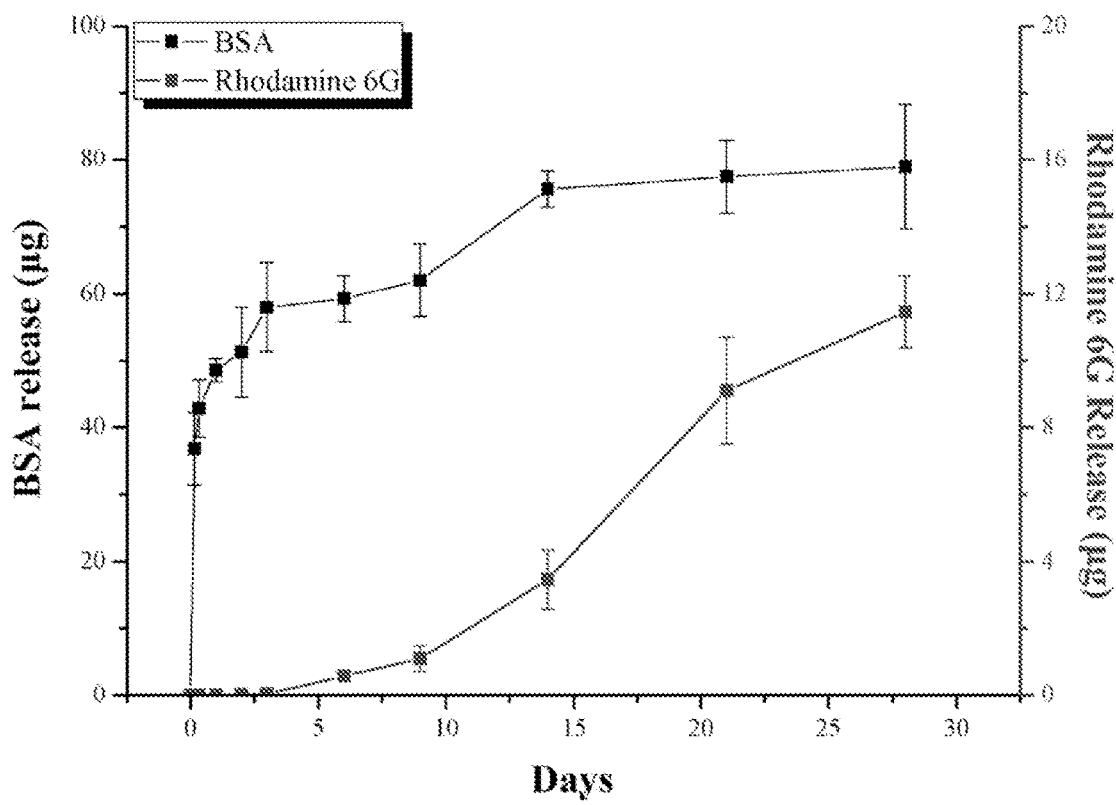

The release of hydrophobic molecules (e.g., paclitaxel) from electrospun nanofiber membranes can last more than 2 months (Xie et al. (2006) Pharm. Res., 23:1817-1826). A mussel-inspired protein-coated nanofiber system for pH-responsive release of doxorubicin has also been demonstrated (Jiang et al. (2014) Acta Biomater., 10:1324-1332). Here, the encapsulation of rhodamine 6G in biodegradable polycaprolactone (PCL) and non-biodegradable polyurethane (PU) nanofiber membranes and rings has been demonstrated. As seen in FIG. 3, the ring structure significantly prolongs the release of hydrophilic molecules (e.g., rhodamine 6G) compared to a membrane.

The release of rhodamine 6G (MW: 479 g/mol, used as a model drug of gemcitabine (MW: 299 g/mol)) from nanofiber-based ring devices was demonstrated to endure for more than 2 months (FIGS. 3 and 4). By modulating the thickness of layers of the electrospun nanofiber (by increasing the volume of polymer solution used during electrospinning), the release rate and the lag time for drug release profiles can be tailored (FIGS. 4 and 5). For example, thicker layers without further incorporating drugs resulted in slower release rates of the drug from the core. FIG. 4 shows the delayed release profiles of rhodamine 6G from PU nanofiber rings by varying the thickness of outer layer (e.g., by volumes of polymer solution). Similarly, the delayed release profiles of rhodamine 6G from PCL nanofibers are shown in FIG. 5.

FIG. 6 shows nanofiber ring devices can release two different molecules in a sequential way. Specifically, rhodamine 6G was loaded on PU nanofibers such that upon rolling/folding of the nanofibers, the rhodamine 6G would be located in the core of a cross-section of the nanofiber ring (FIG. 6B). Conversely, BSA was loaded on PU nanofibers such that upon rolling/folding of the nanofibers, BSA would be located towards the outer surface or shell of a cross-section of the nanofiber ring (FIG. 6B). As seen in FIG. 6C, the BSA was released in an initial burst from the nanofiber rings whereas the rhodamine 6G was delayed in its release and released more slowly over time due to its location in the core of the nanofiber ring.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A nanofiber ring comprising at least one compound, wherein said nanofiber ring comprises at least one rolled tubular nanofiber membrane, and wherein said nanofiber membrane comprises electrospun nanofibers.

2. The nanofiber ring of claim 1, wherein said nanofiber ring comprises at least two different compounds.

3. The nanofiber ring of claim 2 comprising a first compound and a second compound, wherein in a cross-sectional view of the nanofiber ring, the first compound is located towards the core of the nanofiber ring and the second compound is located towards the surface of the nanofiber.

4. The nanofiber ring of claim 2, wherein said first compound and said second compound are in distinct areas of the nanofiber ring in a cross-sectional view.

5. The nanofiber ring of claim 1, wherein said electrospun nanofibers comprise hydrophobic polymers.

6. The nanofiber ring of claim 1, wherein said electrospun nanofibers comprise polycaprolactone.

7. The nanofiber ring of claim 1, wherein said compound is a small molecule.

8. The nanofiber ring of claim 1, wherein said nanofiber ring comprises more than one nanofiber membrane.

9. The nanofiber ring of claim 8, wherein each nanofiber membrane comprises a compound distinct from the compounds of the other nanofiber membranes.

10. The nanofiber ring of claim 8, wherein each nanofiber membrane comprises electrospun nanofibers of a polymer distinct from the polymers of the other nanofiber membranes.

11. A method for producing a nanofiber ring of claim 1, the method comprising:
a) electrospinning nanofibers onto a rotating cylindrical substrate to synthesize a nanofiber membrane,
b) adding at least one compound to the nanofiber membrane, thereby generating a loaded nanofiber membrane, and
c) rolling the loaded nanofiber membrane to generate said nanofiber ring.

12. The method of claim 11, wherein step b) comprises adding the compound during the electrospinning of step a).

13. The method of claim 11, wherein step b) comprises adding the compound after the nanofiber membrane is formed.

14. The method of claim 11, wherein step b) comprises adding the compound evenly throughout the nanofiber membrane.

15. The method of claim 11, wherein step b) comprises adding the compound to distinct locations of the nanofiber membrane.

16. The method of claim 11, further comprising repeating steps a), b), and c) at least once, thereby generating a nanofiber ring or tube comprising more than one nanofiber membrane.

17. A method of treating a disease or disorder in a subject in need thereof, said method comprising administering a nanofiber ring of claim 1 to the subject.

18. The method of claim 17, wherein said disease or disorder is cancer and the compound of the nanofiber ring or tube is an anticancer agent.

19. The method of claim 18, wherein said cancer is pancreatic cancer and said anticancer agent is gemcitabine.

20. The method of claim 18, wherein said administration comprises implanting the nanofiber ring into or near cancerous tissue.

21. A method for sequentially delivering at least two compounds to a subject, said method comprises administering a nanofiber ring of claim 1 to the subject, wherein said nanofiber ring comprises at least a first compound and at least a second compound, wherein said first compound is located towards the core of a cross-section of the nanofiber ring and said second compound is located towards the surface of a cross-section of the nanofiber ring.

22. The method of claim 21, wherein said first and second compounds are in distinct locations within the nanofiber ring.

23. The nanofiber ring of claim 1, wherein the nanofiber ring has a circular cross-section.

24. The nanofiber ring of claim 3, wherein said first compound is contained within the middle 50% by area of the cross-sectional view and said second compound is contained outside of the middle 50% by area of the cross-sectional view.

* * * * *